(12) United States Patent
Liu et al.

(10) Patent No.: US 12,144,491 B2
(45) Date of Patent: Nov. 19, 2024

(54) SPECTRALLY ENCODED IMAGING USING BAND-SHIFTING IMAGING PROBES

(71) Applicant: The Penn State Research Foundation, University Park, PA (US)

(72) Inventors: Zhiwen Liu, State College, PA (US); Jian Yang, State College, PA (US); Yizhu Chen, Fremont, CA (US); Dingbowen Wang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 17/264,161

(22) PCT Filed: Jul. 30, 2019

(86) PCT No.: PCT/US2019/044144
§ 371 (c)(1),
(2) Date: Jan. 28, 2021

(87) PCT Pub. No.: WO2020/028367
PCT Pub. Date: Feb. 6, 2020

(65) Prior Publication Data
US 2021/0228066 A1    Jul. 29, 2021

Related U.S. Application Data

(60) Provisional application No. 62/712,647, filed on Jul. 31, 2018.

(51) Int. Cl.
*G01N 21/64*    (2006.01)
*A61B 1/04*    (2006.01)
(Continued)

(52) U.S. Cl.
CPC .......... *A61B 1/043* (2013.01); *A61K 49/0021* (2013.01); *A61K 49/006* (2013.01);
(Continued)

(58) Field of Classification Search
CPC .......... A61B 1/043; G01N 2021/6419; G01N 2021/6421; G01N 2021/8893
See application file for complete search history.

(56) References Cited

U.S. PATENT DOCUMENTS

2004/0096118 A1* 5/2004 Liang .................. G02B 21/02
                                                    382/284
2007/0081236 A1* 4/2007 Tearney ............. G01B 9/02091
                                                    359/390
(Continued)

FOREIGN PATENT DOCUMENTS

WO    WO-2016164437 A1 * 10/2016 ............. C08G 18/73

OTHER PUBLICATIONS

Hubbard et al. Wide spectral range confocal microscope based on endlessly single-mode fiber, Optics Express vol. 18, No. 18, pp. 18811-18819 (Year: 2010).*

(Continued)

*Primary Examiner* — David P Porta
*Assistant Examiner* — Shun Lee
(74) *Attorney, Agent, or Firm* — DINSMORE & SHOHL LLP

(57) ABSTRACT

A spectrally encoded fluorescence imaging system includes a multi-wavelength excitation light source emitting excitation light for illuminating a sample, optical components for introducing spectral encoding to focus different wavelengths of the excitation light at different positions in the sample to generate fluorescence at different, spatial positions, and band-shifting florescence imaging probes exhibiting excitation-dependent emission band, causing the fluorescence
(Continued)

generated at different spatial positions to exhibit different band shifts, such that image information is encoded in the band-shifted fluorescence spectrums for parallel detection by a spectrometer or arrayed detectors operable to resolve different wavelengths.

19 Claims, 13 Drawing Sheets

(51) Int. Cl.
  *A61K 49/00* (2006.01)
  *G01N 21/88* (2006.01)
(52) U.S. Cl.
  CPC ..... *G01N 21/6428* (2013.01); *G01N 21/6458* (2013.01); *G01N 2021/6419* (2013.01); *G01N 2021/6421* (2013.01); *G01N 2021/6423* (2013.01); *G01N 2021/6439* (2013.01); *G01N 2021/8893* (2013.01)

(56) References Cited

U.S. PATENT DOCUMENTS

| | | |
|---|---|---|
| 2007/0087445 A1 | 4/2007 | Tearney et al. |
| 2008/0192248 A1 | 8/2008 | Carver |
| 2010/0062429 A1* | 3/2010 | Patton ............... C07C 225/34 435/6.1 |
| 2010/0256015 A1 | 10/2010 | Lim et al. |
| 2012/0069332 A1 | 3/2012 | Frankel |
| 2017/0276544 A1* | 9/2017 | Gastaldo .............. G01B 11/022 |
| 2017/0293127 A1* | 10/2017 | Sinha ................ G02B 21/0064 |
| 2018/0088053 A1 | 3/2018 | Yang et al. |

OTHER PUBLICATIONS

International Search Report dated Oct. 29, 2019; International Application No. PCT/US19/44144.

Zhiwei Xie, Jian Yang etc. Synthesis and characterization of citrate-based fluorescent small molecules and biodegradable polymers. Acta Biomaterialia, 2017, 50: 361-369.

* cited by examiner

FIG. 2C
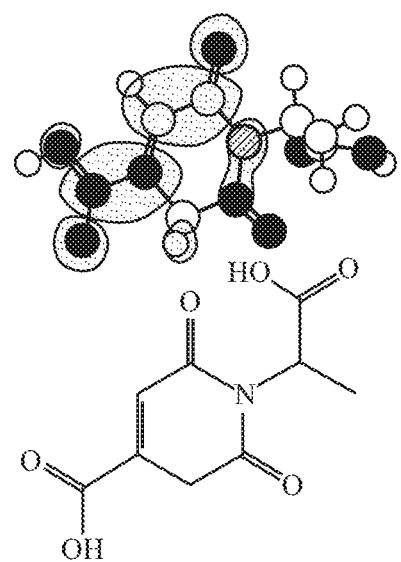
FIG. 2D
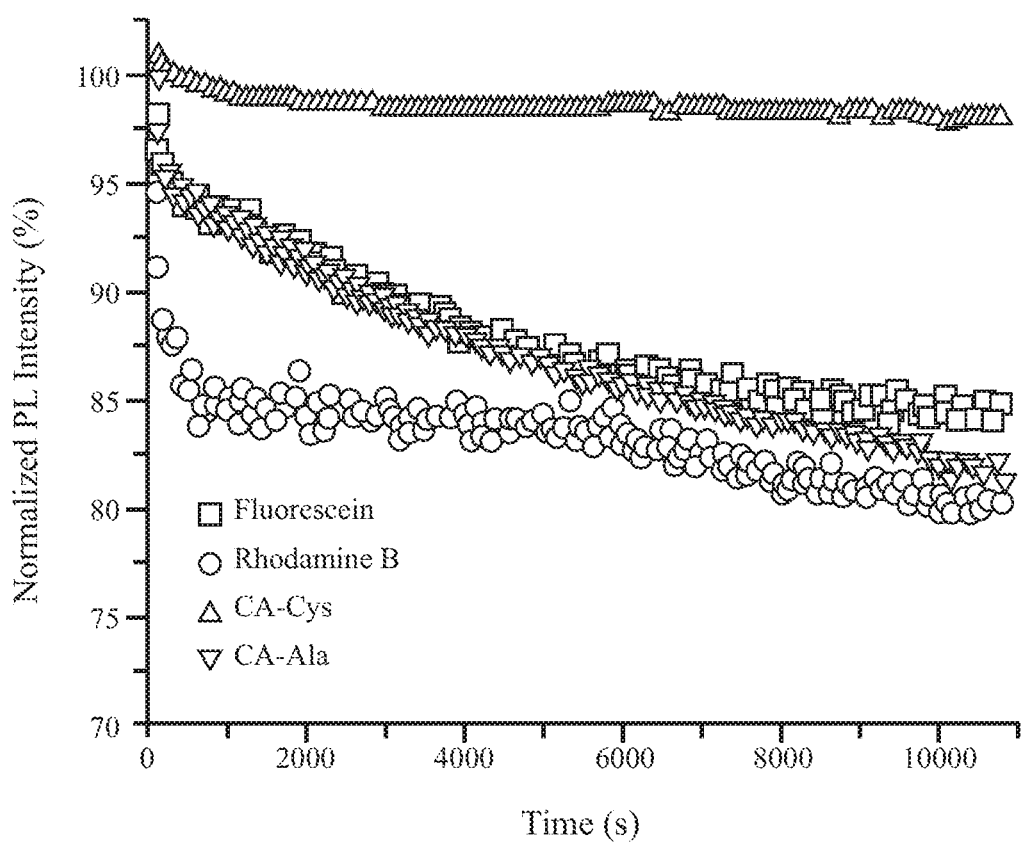
FIG. 2E

FIG. 5C
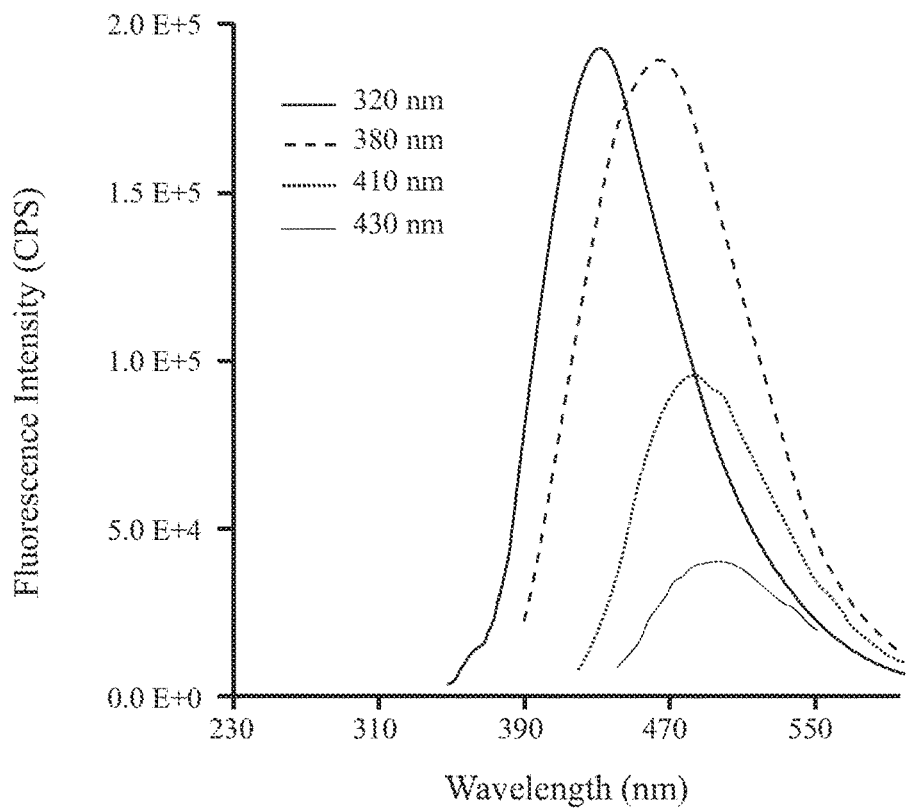
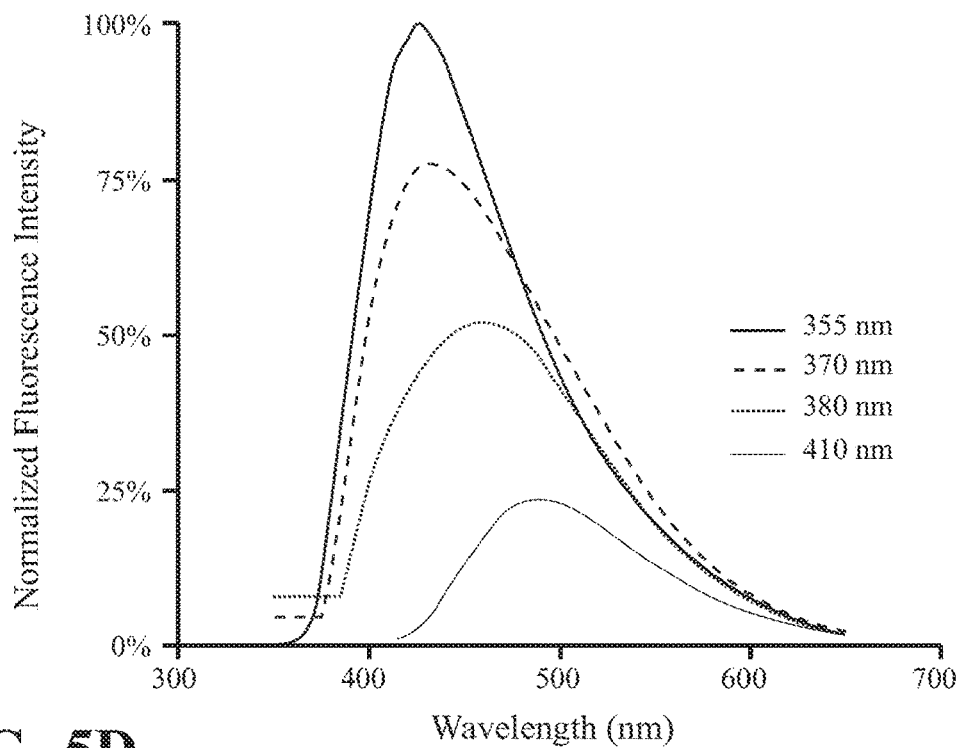
FIG. 5D

FIG. 6E
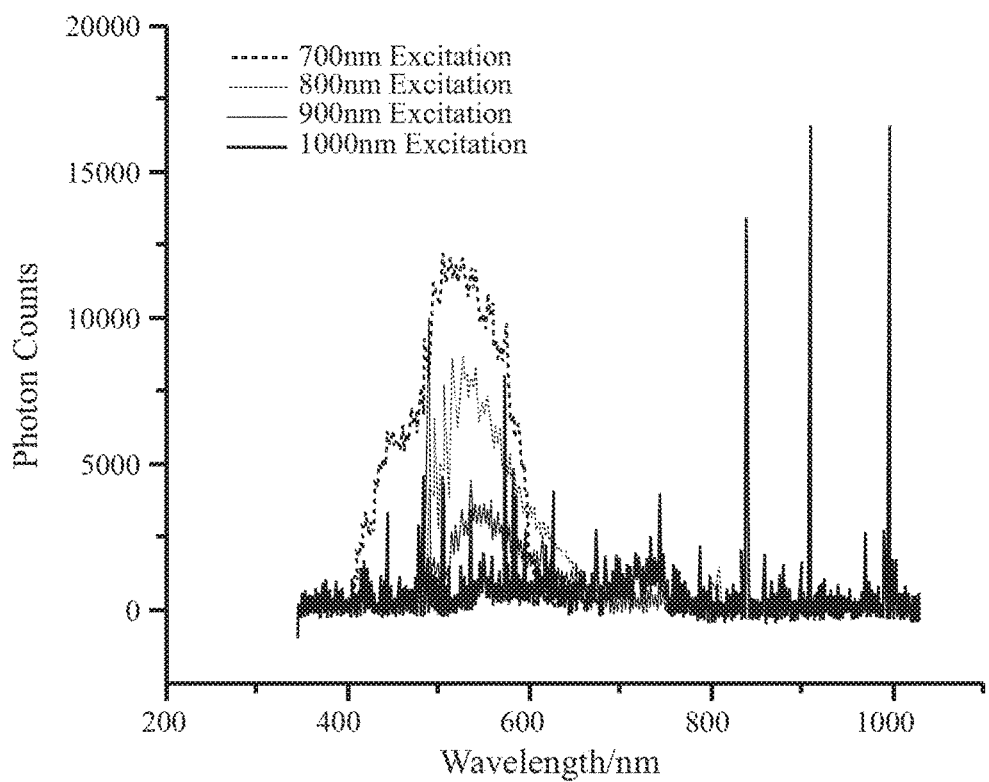
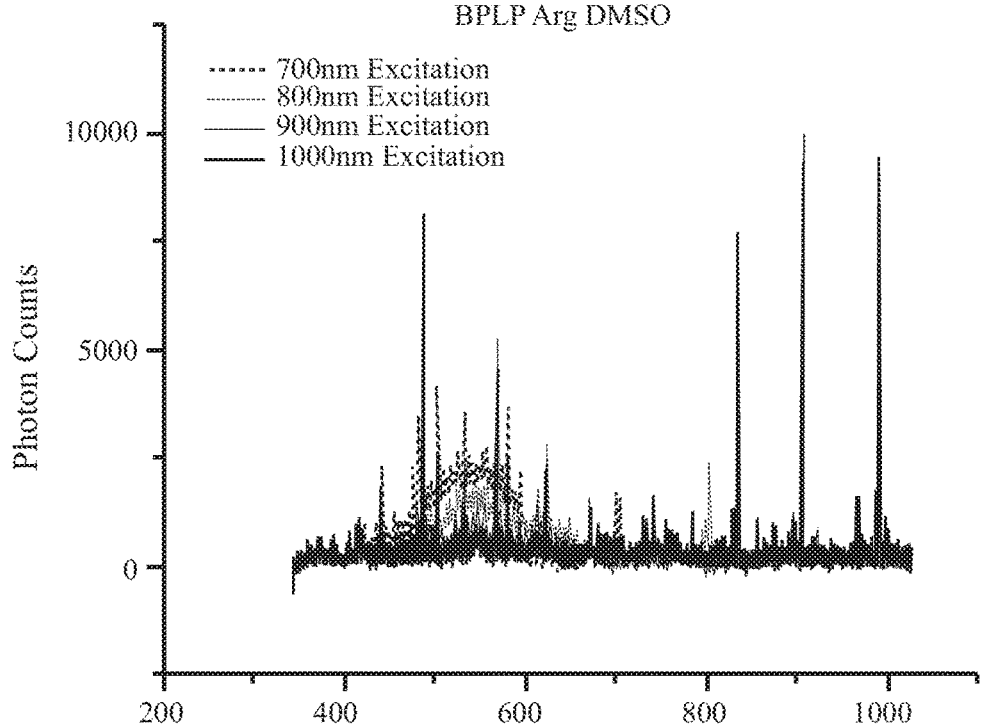
FIG. 6F

SPECTRALLY ENCODED IMAGING USING BAND-SHIFTING IMAGING PROBES

CROSS REFERENCE TO RELATED APPLICATION

This application is the U.S. National Stage of PCT/US2019/044144 filed Jul. 30, 2019, which claims priority from U.S. Provisional Patent Application Ser. No. 62/712,647, filed Jul. 31, 2018, the entire content of both are incorporated herein by reference in their entirety.

GOVERNMENT SPONSORSHIP

This invention was made with government support under Grant No. EB024829 awarded by the National Institutes of Health. The Government has certain rights in the invention.

FIELD OF THE INVENTION

The present invention relates to spectrally encoded imaging using band-shifting imaging probes, specifically, spectrally encoded fluorescence microscopy using band-shifting imaging probes.

BACKGROUND OF THE INVENTION

Laser scanning fluorescence microscopy including multi-photon fluorescence microscopy and confocal fluorescence microscopy is one of the most important imaging modalities, due to its many unique capabilities, such as optical sectioning ability. Fast lateral scanning can be realized by using several techniques such as the Nipkow-type multi-focal point scanning (>1000 frames/s) and rotating polygonal mirror scanning. Yet, axial imaging remains slow, as it typically requires mechanical scanning of either the objective or the specimen, which is slow due to the large inertia that needs to be overcome (e.g., ~10 ms settling time using a state of the art piezo stage), and which can also pose a risk to cause system instability (e.g., vibration, wobbling) and degrade the spatial resolutions. Hence, axial scanning presents a significant limitation for laser scanning microscopy, limiting its capability to image fast processes at multiple depths and in three dimensions, and posing a serious challenge for endoscopic applications where axial scanning is even harder to implement due to the stringent space limitation.

SUMMARY OF THE INVENTION

The present invention provides a method of spectrally encoded fluorescence imaging for imaging a sample. The method combines the concept of mapping excitation light with different wavelengths to different spatial locations and the concept of using band-shifting florescence imaging probes. The band-shifting florescence imaging probes may be fluorophores that exhibit excitation-dependent emission bands. In other words, the band-shifting florescence imaging probes exhibit shifts of fluorescence emission bands as the excitation wavelength is shifted. The merging of the two concepts enables fluorescence image information of a sample by spectrally encoding the excitation and transferring the spectral encoding to the fluorescence signal, thereby enabling fast fluorescence imaging by realizing parallel imaging in the axial direction relative to light beam illuminated on the sample, in the lateral directions relative to light beam illuminated on the sample, or both.

In one example, the fluorophores are biodegradable photoluminescent polymers (BPLPs) or molecular fluorescent probes. In another example, the fluorophores are small molecular citrate-based photoluminescent dyes (CPDs) with identified structures of thiozolopyridine (TPA) and dioxopryridine (DPR). For example, the DPR family can be synthesized by reacting citric acid with non-thiol amine molecules such as L-alanine (CA-Ala).

Band-shifting florescence imaging probes may include polymers or molecules with excitation-dependent property, photostable emission, and cytocompatibility that are suited for parallel fluorescence imaging. A citrate methodology is developed for the development of brightly fluorescent, photostable, and band-shifting organic dyes by reacting citric acid with primary amines. A large pool of available candidates of primary amines enables the fine-tuning and optimization of the photophysical properties of the organic dyes.

The biological sample may be tissues or cells. The tissues or cells may be labeled using band-shifting florescence imaging probes in accordance with the embodiments of the present invention. The band-shifting florescence imaging probes may be conjugated with proteins via common conjugation methods or can be incorporated in polymers and nanoparticles.

In one embodiment, the method of spectrally encoded fluorescence imaging for imaging a biological sample may include labeling the biological sample with band-shifting florescence imaging probes, providing a multi-wavelength excitation light source for excitation of the labeled biological sample, introducing spectral encoding such that the different wavelengths of the excitation light are focused at different spatial positions in the sample thereby generating band-shifted fluorescence at the different spatial positions, and detecting image information encoded in the band-shifted fluorescence spectrums using detectors operable to resolve different wavelengths in parallel, thereby simultaneously recording activities of the biological sample at the different spatial positions.

The detectors may be spectrometers, arrayed detectors or other wavelength-selective detectors.

The spectral encoding may be purposely introduced such that the spatial positions are in the axial direction or lateral direction relative to the excitation light beam impinged on the sample. Chromatic aberration can be introduced using an optical system having a plurality of optical components to realize spectral encoding. The axis of the excitation light may be defined as the axis of the optical system which introduces the chromatic aberration. The axial direction is the direction that coincides or is parallel to the axis of the excitation light. The lateral direction is the direction perpendicular to the axis of the excitation light. In one example, the lateral direction may include two orthogonal directions both of which are perpendicular to the axial direction. Three-dimensional parallel fluorescence imaging may then be achieved. The axial positions refer to the different locations along the axial directions. The lateral positions refer to the different locations along the lateral directions. Longitudinal chromatic aberrations may be introduced such that different wavelengths are focused at different spatial positions in the axial direction. Traverse or lateral chromatic direction can be introduced such that different wavelengths are focused at different spatial positions in the lateral directions. Diffractive optical elements (e.g., gratings, Fresnel lenses), refractive optical elements (e.g., lenses, prims), or a combination of these elements may be used to direct excitation beams of different wavelengths to different spatial positions to realize spectral encoding in three dimensions.

The fluorescence may be generated in multi-photon excitation modality (such as two-photon) or in one-photon excitation modality. The present method can enhance the capability of multi-photon microscopy or one-photon confocal microscopy, enabling simultaneous recording of activities across multiple cells and at different positions in a biological sample.

The present invention also provides a spectrally encoded fluorescence imaging system for imaging a sample. The spectrally encoded fluorescence imaging system may include a multi-wavelength excitation light source emitting excitation light with different wavelengths. The excitation light source may be lasers or LEDs, or other broadband light sources. The excitation light may be processed by optical components for introducing spectral encoding such that the different wavelengths of the excitation light is focused at different spatial positions in the sample thereby generating fluorescence at the different spatial positions. The imaging system may further include detectors operable to resolve different wavelengths for simultaneous detection of the fluorescence at the different spatial positions, thereby enabling simultaneous recording of image information and activities of the sample at the different spatial positions.

The tunability of the imaging system setup matches the excitation/emission properties, thus making the band-shifting florescence imaging probe an integral part of the imaging system. The band-shifting florescence imaging probes may be fluorophores that exhibit excitation-dependent emission bands, thereby causing fluorescence signals generated at the different spatial positions to exhibit different spectral shift or different spectral shape or both, such that image information is encoded in the band-shifted fluorescence spectrums. The biological samples are labeled (e.g., dyed) with the band-shifting florescence imaging probes in order to be imaged.

BRIEF DESCRIPTION OF THE DRAWINGS

FIG. 2C shows a photo of two-photon excited fluorescence;

FIG. 2D shows molecular modeling (computed isosurfaces) and the chemical structure of CA-Ala;

FIG. 2E is a plot showing fluorescence photostability of CA-Cys and CA-Ala with 3 hours continuous excitation at each band-shifting probe's wavelength of maximum excitation;

FIGS. 5A-5G are plots showing one-photon fluorescence emission of several candidate band shifting probes: (A). CA-Ser; (B). CA-Ser purified; (C). CA-Asp Acid; (D). CA-Ala; (E). BPLP-Arg; (F). CA-Tu; (G). CASer-Urea;

FIGS. 6A-6H are plots showing two photon fluorescence emission of different probes at 700 nm-1000 nm excitation wavelengths; (A). CA-Ser; (B). CA-Ser purified; (C). CA-Asp; (D). CA-Ala; (E). CA-Ala base; (F). BPLP-Arg DMSO.

DETAILED DESCRIPTION OF THE INVENTION

Overview of the Invention

The present invention provides spectrally encoded fluorescence microscopy using spectrally encoded excitation (e.g., by using chromatically aberrated excitation light) and a spectrally encoded fluorescence signal through the use of band-shifting fluorescence imaging probes. Band-shifting florescence imaging probes refer to fluorophores that exhibit an excitation-dependent emission band, i.e., shifts of fluorescence emission band as the excitation wavelength is shifted. Traditional fluorophores such as Rhodamine B and fluorescein do not exhibit band-shifting properties. The spectrally encoded excitation refers to excitation light with different wavelengths that is focused at different locations on a sample to be imaged. In one example, the spectrally encoded excitation is achieved by chromatic aberration.

The merging of the two concepts of spectrally encoded excitation and band-shifting imaging probes can enable fast fluorescence imaging by potentially eliminating scanning in the axial direction, in lateral directions, or both.

The technique of embodiments of the present invention may be used in multi-photon microscopy and one-photon confocal microscopy. The multi-photon (e.g., two-photon) microscopy in accordance with the present invention can potentially improve the axial scanning speed by 10×. The concept of the present invention will be described here in detail using two-photon microscopy as an example. The method is also applicable or can be extended to other multi-photon modalities and to a one-photon fluorescence imaging modality.

Figure 1:
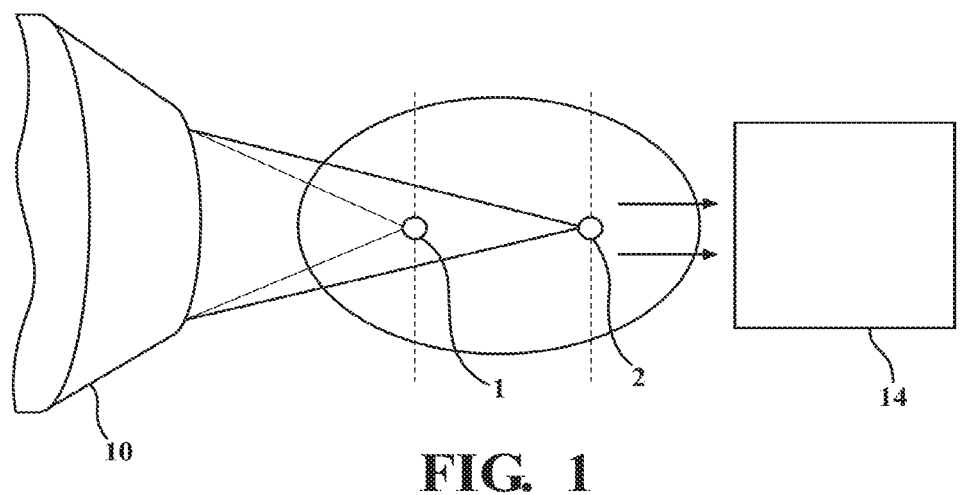
FIG. 1 is a schematic showing the concept of the present invention.

As illustrated in FIG. 1, excitation light with different wavelengths from an excitation source 10 is first focused at different axial positions 1, 2 through purposely-introduced chromatic aberration.

If using traditional fluorophores, the emission band would be the same regardless of the excitation wavelengths as long as the excitation wavelengths are sufficient to cause the excitation to occur. Embodiments of the present invention instead uses band-shifting fluorescent probes to let the two-photon fluorescence excited by different wavelengths exhibit a wavelength shift, termed band shift, so that they can be imaged in parallel by using a spectrometer, or generally, arrayed detectors that can resolve different wavelengths, e.g., by using filters. Since chromatic aberration caused the excitation light with different wavelengths to be focused at different locations, and therefore fluorescence excited by different wavelengths is generated at different locations, the axial image information is thus encoded in the band-shifted fluorescence spectrums for parallel detection. If the chromatic aberration causes the excitation light with different wavelengths to be focused at different axial positions, then axial scanning of the sample to be imaged may be avoided within the achievable axial range of the spectrally encoded excitation. If the chromatic aberration causes the excitation light with different wavelengths focused at different lateral positions, then lateral scanning of the sample to be imaged may be avoided within the achievable lateral range of the spectrally encoded excitation. Axial scanning or lateral scanning can be used in conjunction of the spectral encoding to further increase the axial or lateral imaging range.

As shown in FIG. 1, the excitation wavelengths are first mapped to different spatial locations by purposely introduced and controllable chromatic aberration, or other spectral encoding methods making use of diffractive optical elements, refractive optical elements, or a combination of these optical elements. For example, the locations 1 and 2 show different axial positions. This wavelength-space mapping or encoding is then transferred to the fluorescent signal through the use of the band-shifting imaging probes, which have high photostability and can continuously shift its emission band as the excitation wavelength varies. For example, the emission band corresponding to location 1 and the emission band corresponding to location 2 will have different center wavelengths or spectral shapes or other spectral features so that the imaging signals at different axial positions can be measured at the same time and be distinguished. During spectrally encoded imaging of a sample, various excitation wavelengths would be mapped to various positions, such as various axial positions. A band of excitation light would then be mapped to a range of axial positions or depths within the sample. The fluorescence emissions at the various locations may then be detected and collected by a detector 14. The detector may be a spectrometer or arrayed wavelength-resolving detectors.

This configuration of having different excitation wavelengths focused at different positions to excite fluorescence (multi-photon or one-photon excitation) exhibiting different band shifts, which are detected in parallel by a spectrometer, or an array of filters and detectors, or other wavelength-selective detectors, enables parallel fluorescence imaging. This is analogous to the way that multiple wavelength channels are used to carry digital bits information in parallel in an optical fiber (i.e., wavelength division multiplexing). By parallelizing axial imaging or lateral imaging, the technique of the present invention can expand the capability of fluorescence imaging, including multi-photon excitation fluorescence imaging or confocal fluorescence imaging for monitoring fast biological processes as well as enabling micro-endoscopic imaging of tissue.

The present method can enhance the capability of scanning fluorescence microscopy and open new possibilities for monitoring fast processes, such as in vivo two-photon imaging of neuronal networks and cardiomyocytes, and particularly for applications requiring the simultaneous recording of activities across multiple cells and at different axial positions. Since it is especially challenging to implement fast mechanical scanning within a confined space in an endoscopy setting, the present method, with the ability to potentially image up to hundreds of microns deep into tissue without the need of axial mechanical scanning, can enable miniature micro-endoscopy for early cancer diagnosis. Specifically, colorectal cancer is the third leading cause of cancer deaths in the US, with over 146,970 new cases each year and more than one third leading to fatality largely due to diagnosis at late and incurable stages. The band-shifting imaging probes can be conjugated with an anti-epidermal growth factor receptor (anti-EGFR) antibody for early colorectal cancer targeting. The ability of depth/axial imaging is crucial for guiding biopsy and surgery, e.g., determining where and, critically, how deep cancerous tissues or tumor micro-foci (invisible to surgeon's naked eyes but visible under fluorescence endoscopic imaging) should be removed.

Figure 2A:
FIG. 2A shows images of a band shifting fluorescence probe—BPLP-Ala solution—at increasing excitation wavelengths from left to right.
Figure 2B:
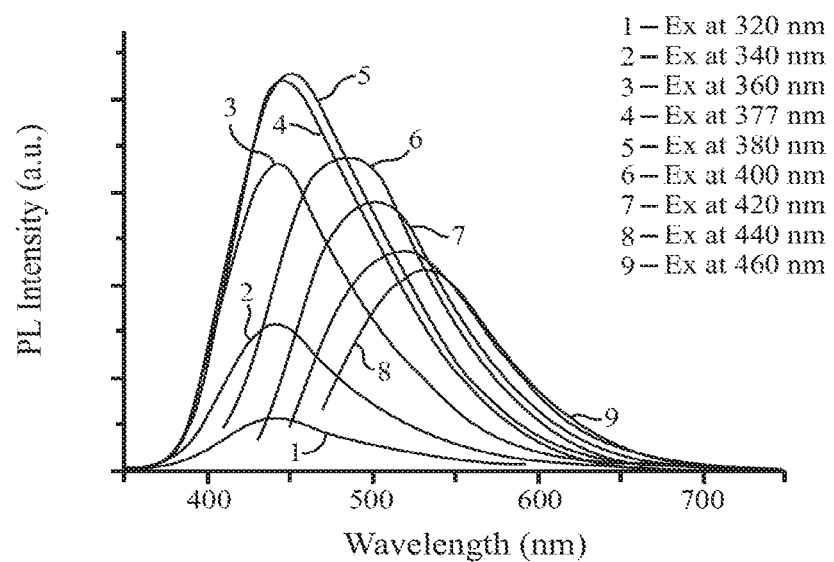
FIG. 2B is a plot showing the one-photon excitation-dependent emission of BPLP-Ala in water.

Band-Shifting Imaging Probes and Cell Labeling Using Band-Shifting Imaging Probes The band-shifting imaging probes for use with embodiments of the present invention will now be described in detail. Cytocompatible BPLPs (biodegradable photoluminescent polymers) and molecular fluorescent probes that exhibit excitation wavelength dependent fluorescence band shifting are developed. BPLPs are synthesized from natural chemicals, including citric acid (CA), natural α-amino acids, and aliphatic diols through a cost-effective condensation reaction. BPLPs are the first polymers to show tunable and inherent photostable fluorescence. Two families of small molecular photostable citrate-based photoluminescent dyes (CPDs) with identified structures of thiozolopyridine (TPA) and dioxopryridine (DPR). DPR structures have been found to show tunable fluorescence. FIG. 2A shows images of the BPLP-Ala solution at increasing excitation wavelengths from left to right. FIG. 2B is a plot showing the one-photon excitation-dependent emission of BPLP-Ala in water. FIG. 2C shows a photo of two-photon excited fluorescence.

The DPR family that are synthesized by reacting citric acid with non-thiol amine molecules such as L-alanine (CA-Ala) possess relatively high quantum yields (22%) and excitation-dependent band shifting behavior. FIG. 2D shows molecular modeling (computed isosurfaces) and the chemical structure of CA-Ala. The band-shifting mechanism of DPRs can be explained as the n-π* and n-σ* transitions of the lone pair electrons of the tertiary amine undergo a red-shift due to the electron withdrawing effects of the adjacent carbonyl groups. Molecular modeling supports that both electron-withdrawing carbonyl groups extend resonance from the tertiary amine, as depicted in the computed isosurfaces in FIG. 2D, resulting in a red shift of absorbance from a smaller highest occupied and lowest unoccupied molecular orbital (HOMO-LUMO). The band-shifting phenomenon is ascribed to the "red edge effect", where the presence of rotating auxochromic groups generates additional dipole interactions between the fluorophore and solvent (water or organic solvent) during intersystem relaxation. The band-shifting properties make DPR (for example, CA-Serine) uniquely suitable for the spectrally encoded fluorescence microscopy. Studies also show that both CA-Cys (TPA, when L-Cysteine was used to react with CA) and CA-Ala (DPR) show much higher photostability compared to traditional organic dyes such as Rhodamine B. FIG. 2E is a plot showing fluorescence photostability of CA-Cys and CA-Ala with 3 hours continuous excitation at each band-shifting probe's wavelength of maximum excitation. Fluorescein and Rhodamine B were used as controls. DPR-based dyes and polymers also showed excellent cytocompatibility both in vitro and in vivo and have been used as effective imaging probes for cell labeling and protein conjugation via common conjugation methods such as 1-ethyl-3-(3-dimethylaminopropyl) carbodiimide (EDC)/Nhydroxysuccinimide (NHS) chemistry. These results support that the DPR dyes can be broadly used for diversified applications due to their easy conjugation/modifications. With the unique excitation-dependent and photostable emission property and excellent cytocompatibility, DPRs are suited for the parallel fluorescence imaging. Selecting different amine-containing molecules for DPR syntheses allow fine-tuning of the photophysical properties of the dyes for imaging optimization.

A citrate methodology is established for the development of brightly fluorescent, photostable, and band-shifting organic dyes by reacting citric acid with primary amines. Representatively, small molecular DPRs are synthesized by adding citric acid (or tricarballylic acid, succinic acid) and L-alanine in a 1:1 molar ratio into 10 mL DI water. The reaction is conducted at 140° C. under vacuum for 4 hours and terminated by adding cold DI water. The resultant DPRs are purified by preparative HPLC with a Shimadzu HPLC system equipped with a C18 column and a fraction collector. To optimize the photophysical properties of the band-shifting DPRs, primary amines are chosen from a large pool of available candidates such as all 20 alpha-amino acids except L-cysteine and many other primary amine molecules including but not limited to γ-Aminobutyric acid, propylamine, ethylenediamine, ethanolamine, phenylenediamine, and hexamethylenediamine. The rich available primary amine molecules enable optimization of the photophysical properties of the DPRs. Note that quantum yield >80%, single-photon excitation wavelength from 250 nm to 600 nm, large fluorescence band shifting from 350 nm to 700 nm, and <10% fluorescence loss after 3 hr continuous excitation have already been achieved.

For cellular labeling, EGFR-expressing colon cancer cell lines are chosen and HT-29 and DLD-1 cells are labeled with DPR molecules (dyes). The carboxyl groups on DPR molecules, as shown in FIG. 2D, will first be activated by ethyl-3-dimethyl amino propyl carbodiimide (EDC) followed by a reaction with anti-EGFR antibody (Amgen). The resulting DPR-anti-EGFR will be purified by dialysis and then freeze-drying. The colon cancer cells will be labeled with band-shifting dyes at various concentrations by incubating the cells with DPR-anti-EFGR for 2 hrs. The DPR-labeled cells will then be washed by phosphate buffer saline (PBS) three times to remove unreacted DPR-anti-EGFR and be used for the imaging hereinbelow.

Spectrally Encoded Imaging Using Band-Shifting Imaging Probes

Design and Development of the Chromatic Two-Photon Imaging System

Figure 3:
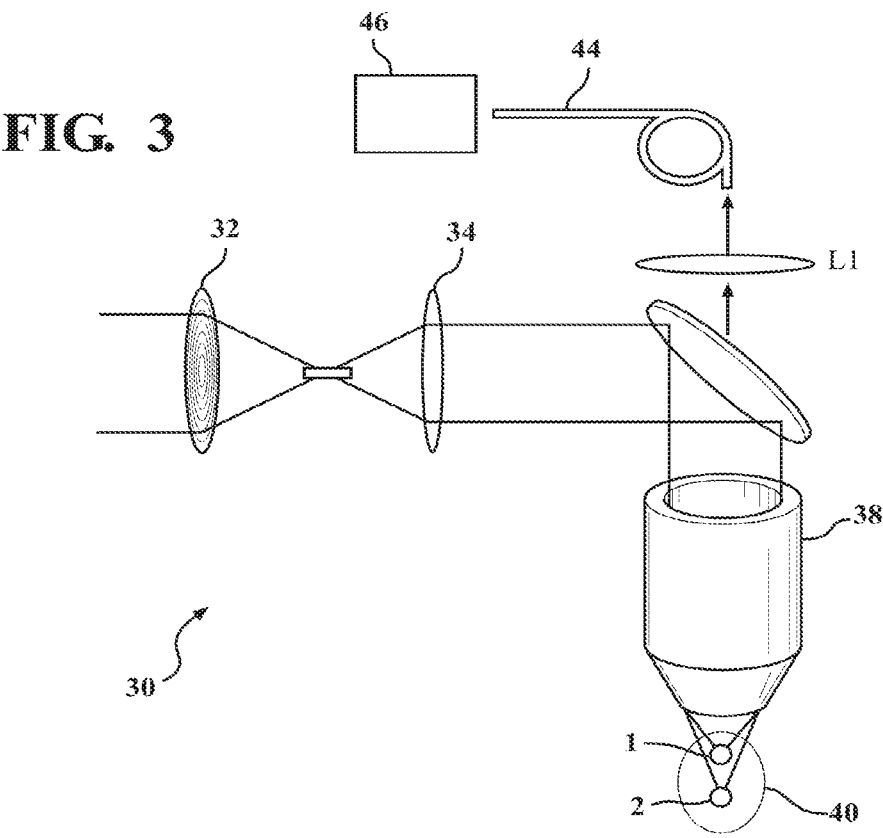
FIG. 3 is a schematic of a spectrally encoded chromatic two-photon imaging system using band-shifting probes in accordance with an embodiment of the present invention.

FIG. 3 provides a schematic of a spectrally encoded chromatic two-photon imaging system 30 according to an embodiment of the present invention. As illustrated in FIG. 3, a Fresnel lens 32, whose focal length is inversely proportional to the wavelength, is used to focus different wavelengths of the excitation beam to different axial positions. A relay lens 34 and an objective 38 are then used to map the chromatically encoded excitation beam onto a sample 40, while achieving the desired spatial resolution and axial imaging range. The two-photon fluorescence is excited at different axial positions by different wavelengths. For example, the excitation beams are focused to different locations 1, 2 in the sample 40. The fluorescence excited at the locations 1, 2 have different center wavelengths (band shifts) because of the different excitation wavelengths. Then, by using the band-shifting imaging probes in accordance with the present invention, the resulted band-shifted fluorescence spectrum is also encoded and varies for different axial positions. Parallel axial imaging can thus be realized by capturing the fluorescence spectrums with a spectrometer or arrayed detectors 46. A multi-mode fiber 44 may be used to collect the fluorescence emissions from the different locations of the sample 40.

The bandwidth of a femtosecond laser (Spectra Physics Tsunami, ~1.7 W) may first be broadened by using a nonlinear fiber (e.g., 700 nm-1.3 μm), to match the two-photon excitation bandwidth of the imaging probes. The resulted broadband excitation beam can then be coupled into the imaging system shown in FIG. 3.

The effective chromatic axial imaging range is given by $$\Delta z = \frac{\Delta \lambda}{\lambda_c} f_0 \frac{1}{n} \left(\frac{f_{oL}}{f_r}\right)^2,$$

where $\Delta\lambda$ is the excitation bandwidth, $\lambda_c$ is the center wavelength, $f_0$, $f_r$, $f_{oL}$ is the focal length of the Fresnel lens (at $\lambda_c$), the relay lens, and the excitation objective (cf. FIG. 3), respectively, and n is the refractive index of the specimen. For example, an axial imaging range of more than 150 μm can be obtained by carefully optimizing the system (e.g., $\Delta\lambda$~200 nm, $\lambda_c$=800 nm, $f_0$=10 cm, $f_r$=2 cm, $f_{oL}$=2 mm, n=1.4). For a wavelength separation of $$\delta\lambda = \frac{n^2 \lambda_c^2}{f_0 NA^2}\left(\frac{f_r}{f_{oL}}\right)^2$$

the resulted axial chromatic aberration is equal to the depth of focus at the sample $$\left(\delta z = \frac{n\lambda_c}{NA^2}\right),$$

where NA stands for the numerical aperture of the objective. Therefore, the excitation spectrum can be discretized using a step of $\delta\lambda$ so that the chromatic aberration within each wavelength channel can be neglected. The intensity distribution of the ith channel can be approximated by $s_i(t)f_i(\vec{r})$, where $s_i$ and $f_i$ stand for the temporal and spatial pulse profile respectively. The two-photon fluorescence signal is thus given by $I(\Lambda)=\Sigma_i c(z_i, \Lambda)N(z_i)\sigma_{TPE}(\lambda_i) g(\lambda_i, \Lambda)(s_i^2(t)\!\!>\!\!(\iiint f_i^2(\vec{r})dV)$, where $\Lambda$ represents the fluorescence wavelength, $\lambda_i$ is the center wavelength of the ith excitation wavelength channel, $\sigma_{TPE}(\lambda_i)$ is the two-photon action cross section, $g(\lambda_i,\Lambda)$ is the normalized two-photon fluorescence spectral line shape function when excited at $\lambda_i$, $N(z_i)$ is the density of the fluorescent imaging probe at depth $z_i=z_0+i\delta z$ where the ith wavelength channel focuses ($z_0$ being a reference position), and $c(z_i, \Lambda)$ is the fluorescence collection efficiency function of the system. For example, by assuming a constant collection efficiency and an ideal excitation source with equal power and nearly identical spatial profile for all wavelength channels, we have $I(\Lambda)\propto\Sigma_i\sigma_{TPE}(\lambda_i) g(\lambda_i, \Lambda)N(z_i)$. If $g(\lambda_i, \Lambda)$ is narrow then a measurement of the fluorescence spectrum directly maps out $N(z_i)$ to achieve parallel axial imaging, similar to the chromatic second harmonic imaging. In the general case, the relationship can be written in a matrix form $I_j=\Sigma_i M_{ji}N_i$, where $I_j\equiv I(\Lambda_j)$, $N_i\equiv N(z_i)$, and M stands for the measurement matrix that also takes into account the collection function, source power and spatial distribution for all the channels, which can be pre-calibrated. This matrix equation can be inverted in the least square sense $N=(M^T M)^{-1}M^T I$ or by using other inversion algorithms. Compressive sensing can be used to improve the axial resolution of the high-throughput modality.

Figure 4A:
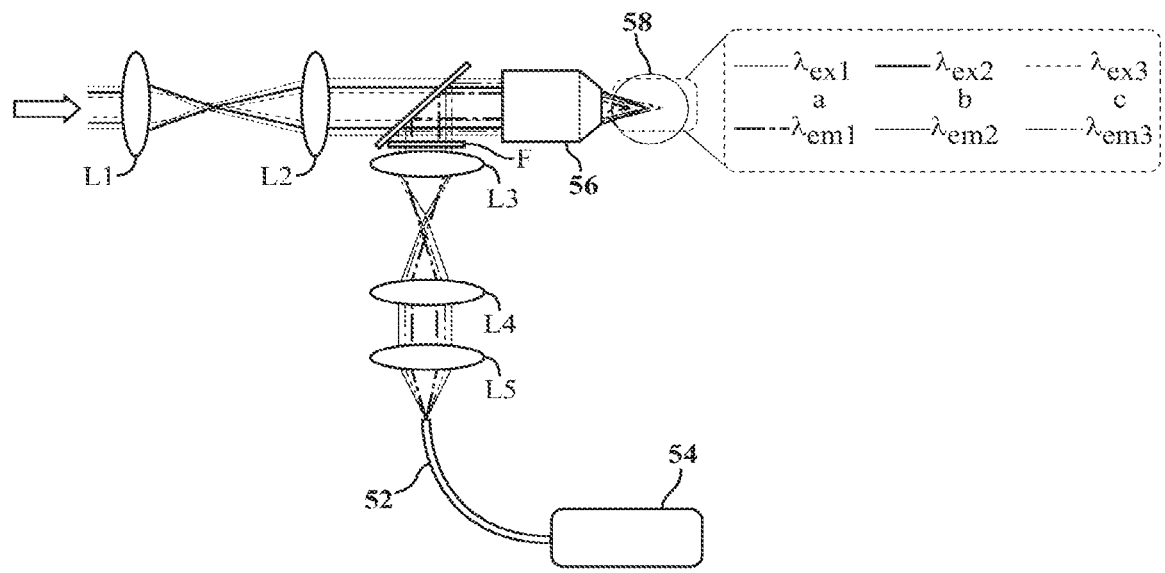
FIG. 4A is a schematic of a spectrally encoded confocal fluorescence imaging system using band-shifting probes in accordance with an embodiment of the present invention.

Design and Development of One-Photon Chromatic Fluorescence Imaging:

FIG. 4A depicts an exemplary embodiment of a one-photon chromatic fluorescence imaging system using the band shifting imaging probes and three excitation wavelengths. The sample will be simultaneously illuminated by multi-wavelength excitation light, which may come from multiple lasers or LED light sources filtered by using filters with desired transmission bands. Singlet lenses, $L_1$ and $L_2$, introduce chromatic aberration upon excitation with three chosen wavelengths. Excitation light at the three wavelengths is focused onto three different axial positions a, b, c of the sample 58 by an achromatic objective lens 56, for example, with the shorter wavelength at the nearer end and the longer wavelength at the further end. The excitation light of different wavelengths excites band-shifted fluorescence. In this embodiment, the fluorescence signal generated at the three depths is collected by the same objective lens, filtered by a filter F, and collimated by using the chromatic aberration introduced from a second pair of singlet lenses L3, L4. A following achromatic lens L5 focuses the collimated fluorescence into a single-mode fiber 52, which serves the function of a pinhole as in a confocal microscope to realize simultaneous confocal imaging at multiple depths. A spectrometer 54, or an array of filters and detectors, or an array of other wavelength-selective detectors, is used to detect the fluorescence signal. Note that the measured spectrum is a combination of fluorescence excited by each excitation wavelength, as given in Equation 1.

$$M = (a_1, a_2, a_3) \cdot \begin{pmatrix} X_1 \\ X_2 \\ X_3 \end{pmatrix} \qquad \text{Equation (1)}$$

where M is the measured spectrum, $a_i$ represents the fluorescence intensity at the ith depth level and $X_i$ is the emission spectrum under the ith excitation wavelength. The fluorescence intensity at the three axial depths can then be retrieved by inverting Equation 1, for example, by using the least squares algorithm. Thus, imaging at three different axial positions can be obtained in parallel.

The achievable axial imaging range within the sample is determined by the chromatic aberration from $L_1$ and $L_2$. Assuming $L_1$ and $L_2$ are made of the same material, the relative axial position distance $\Delta z$, at which the shortest and longest excitation wavelengths are focused, is given by $$\Delta z = \frac{|\delta n|}{n-1}(F_1 + F_2)\frac{F_{obj}^2}{n_m F_2^2} \qquad \text{Equation (2)}$$

where $F_i$ is the focal length of the lenses, n is the refractive index of the lens material, and $\delta n$ is the refractive index difference of lens material between the short wavelength and the long wavelength, $F_{obj}$ is the effective focal length of achromatic objective lens, and $n_m$ is the refractive index of the immersion medium. The nominal focal lengths of $L_1$ and $L_2$ can thus be determined from the desired axial imaging range.

To enable confocal fluorescence detection, the chromatic aberration from the second lens pair, $L_3$ and $L_4$, is used to collimate the fluorescence generated at different axial positions within the sample. In order to find the desired focal lengths and lens materials for the four singlet lenses, ray tracing based on the ABCD matrix method can be performed. In the simulation, two assumptions have been made. First, the excitation beam incident on $L_1$ is collimated. Second, the fluorescence that can be collected by the objective has the same numerical aperture as the focused excitation beam.

Figure 4B:
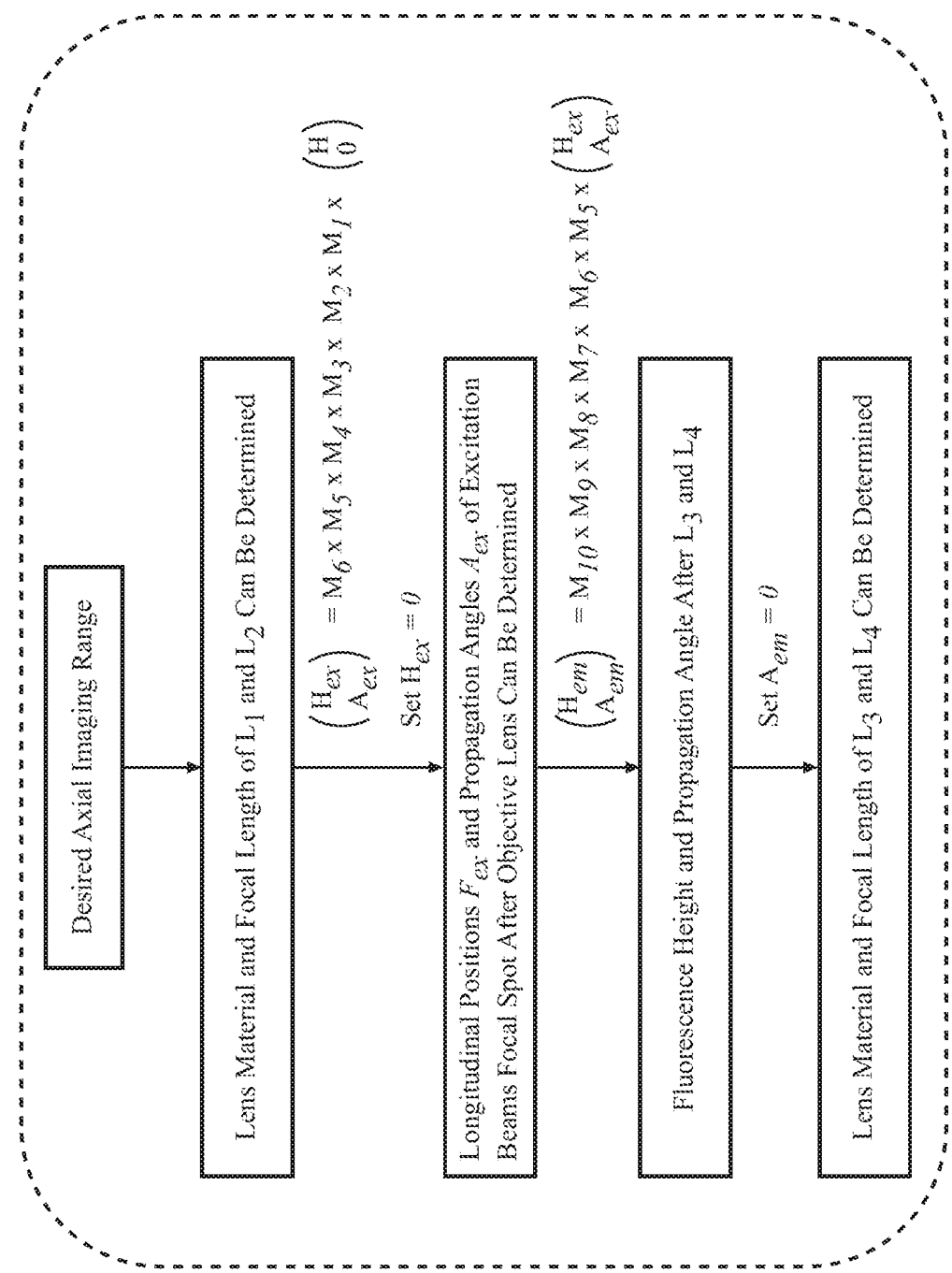
FIG. 4B is a flow chart for the determination of lens material and focal lengths in the design of a spectrally encoded confocal fluorescence imaging system using band-shifting probes in accordance with an embodiment of the present invention.
Figure 5A:
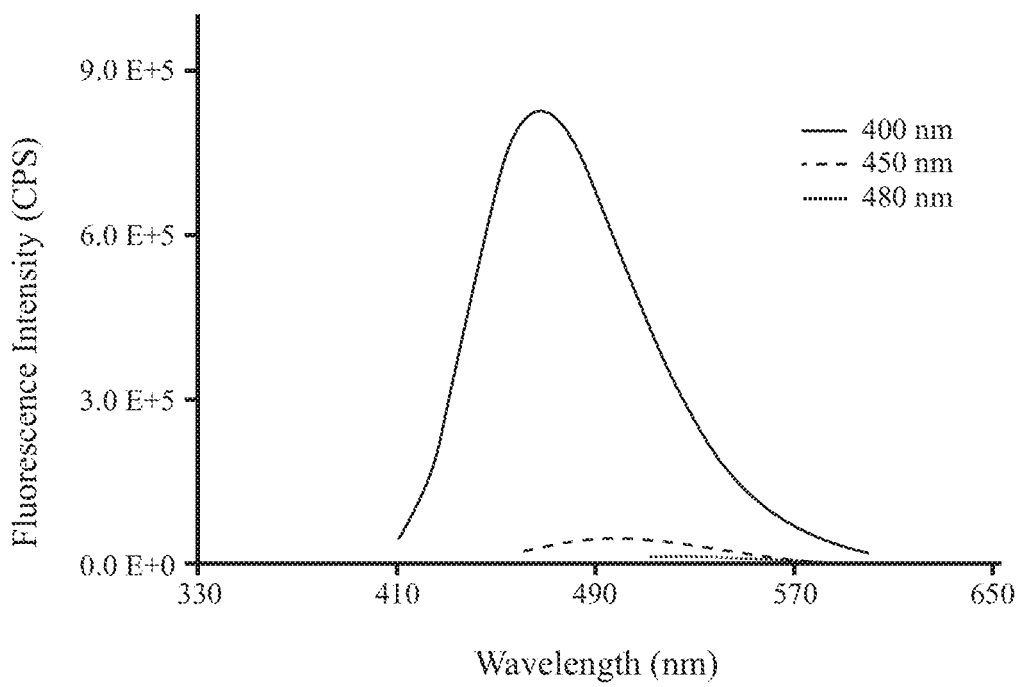
Figure 5B:
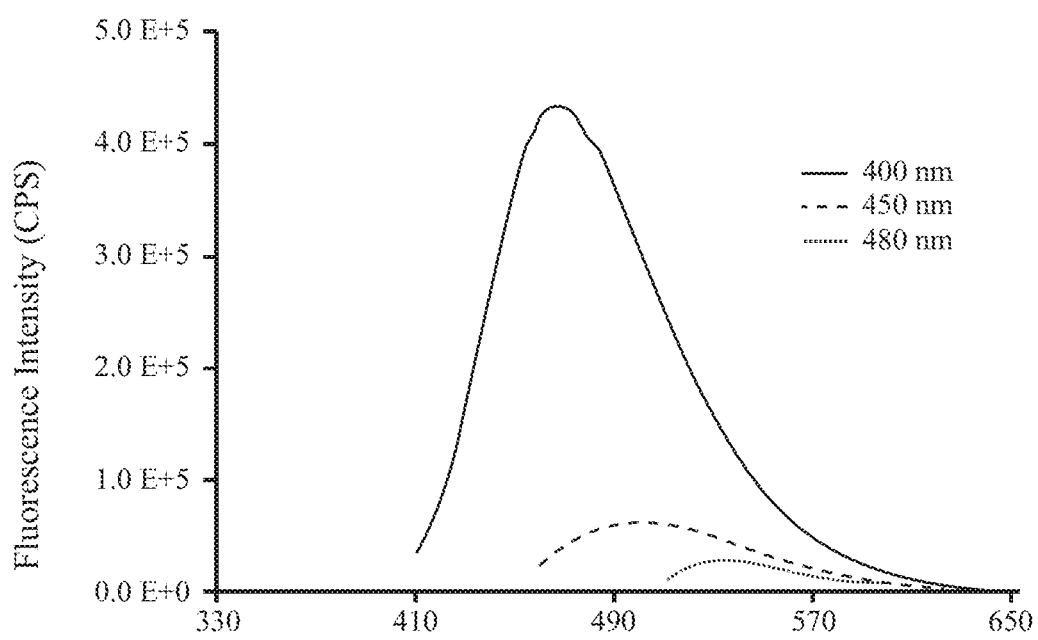
Figure 5E:
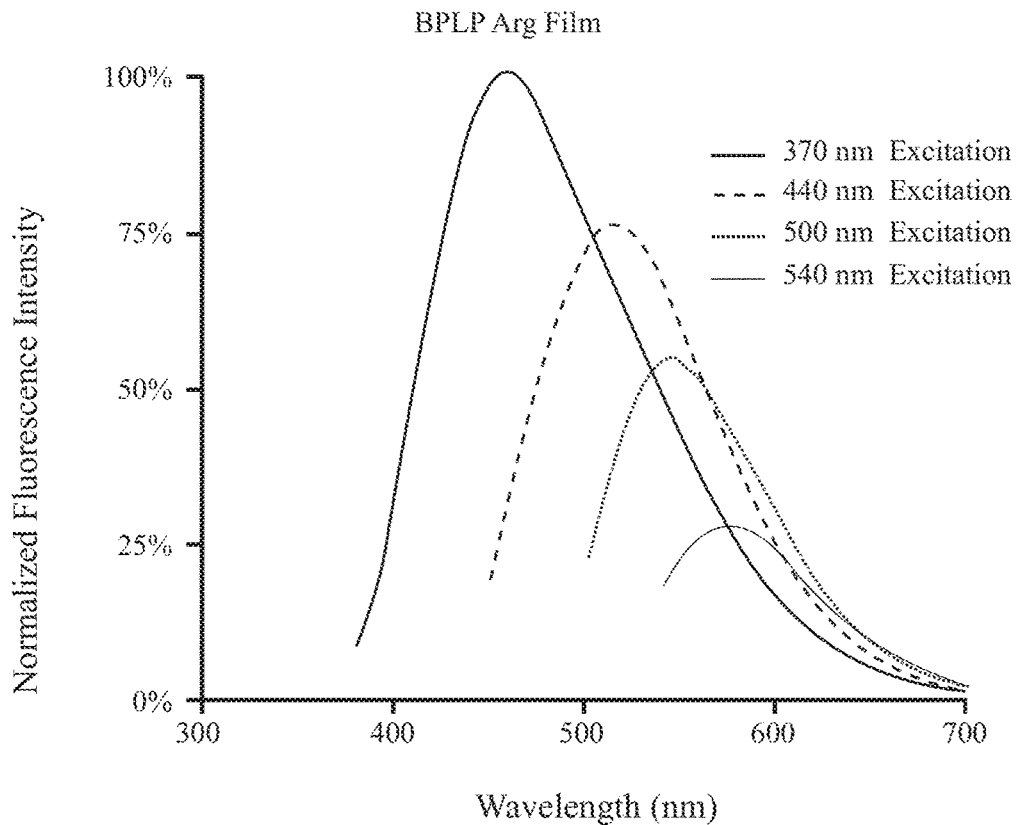
Figure 5F:
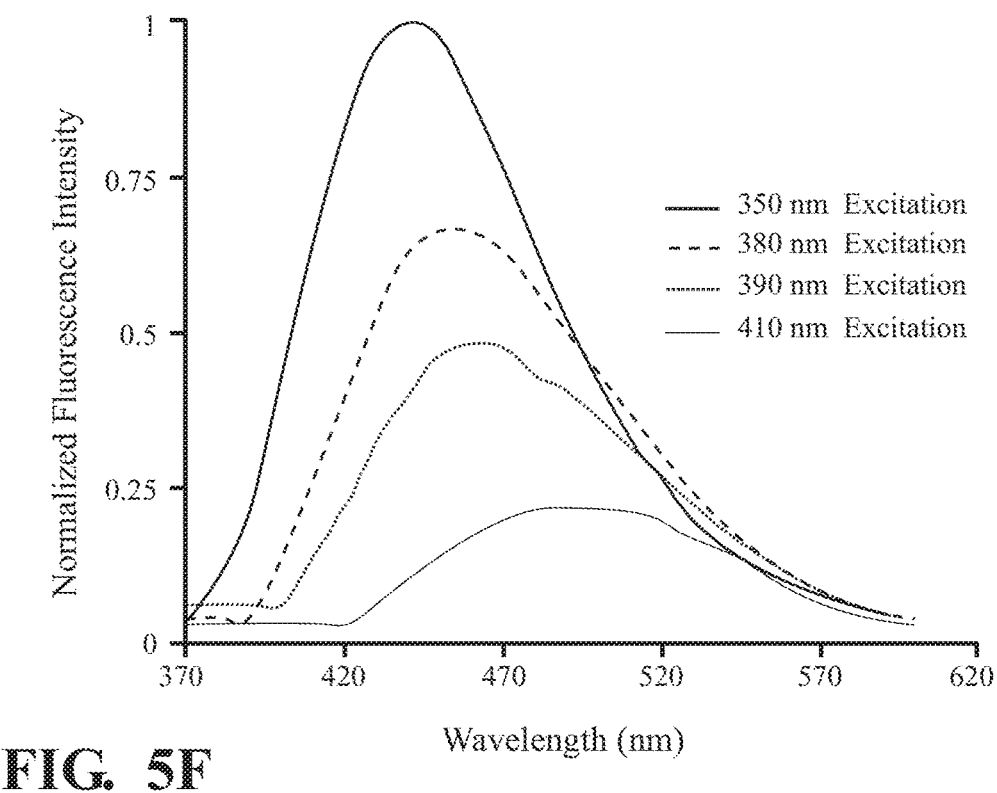
Figure 5G:
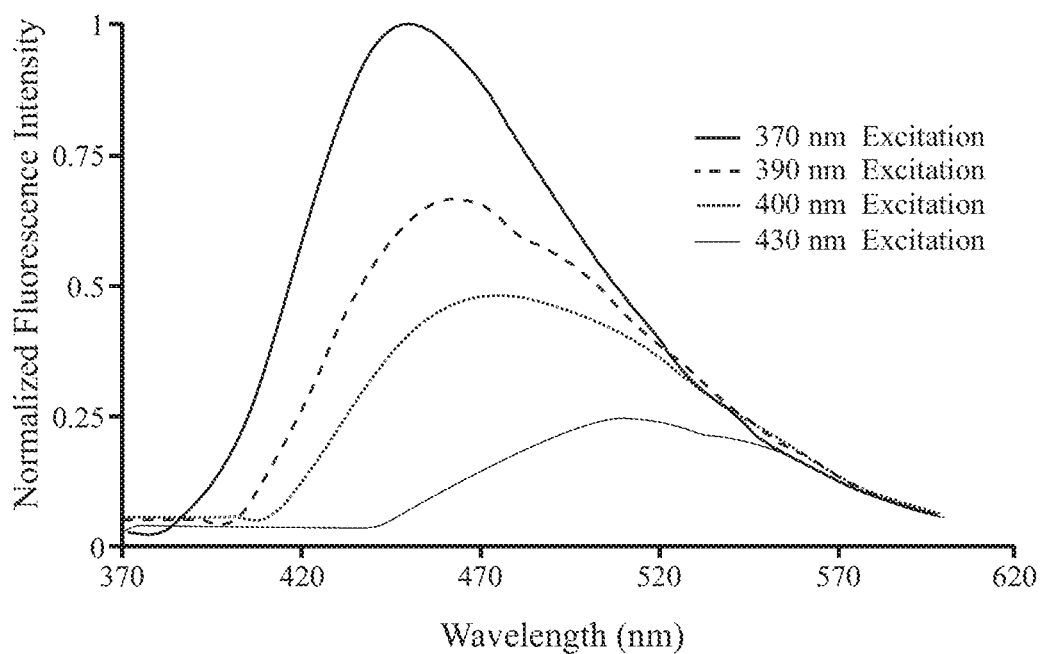
Figure 6A:
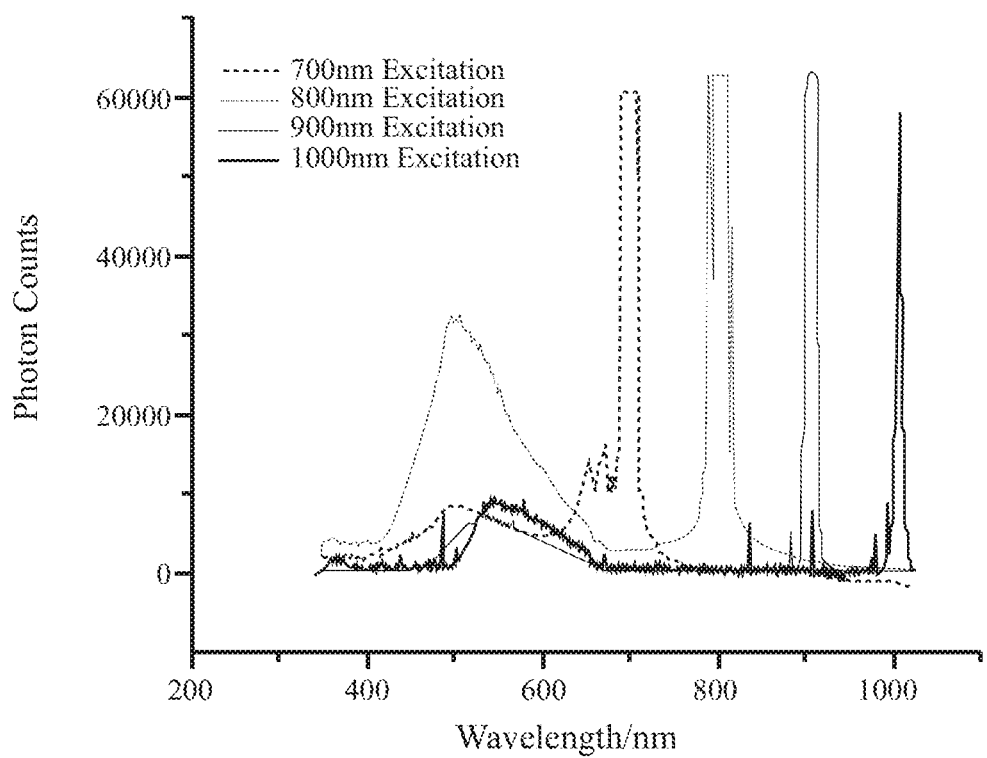
Figure 6B:
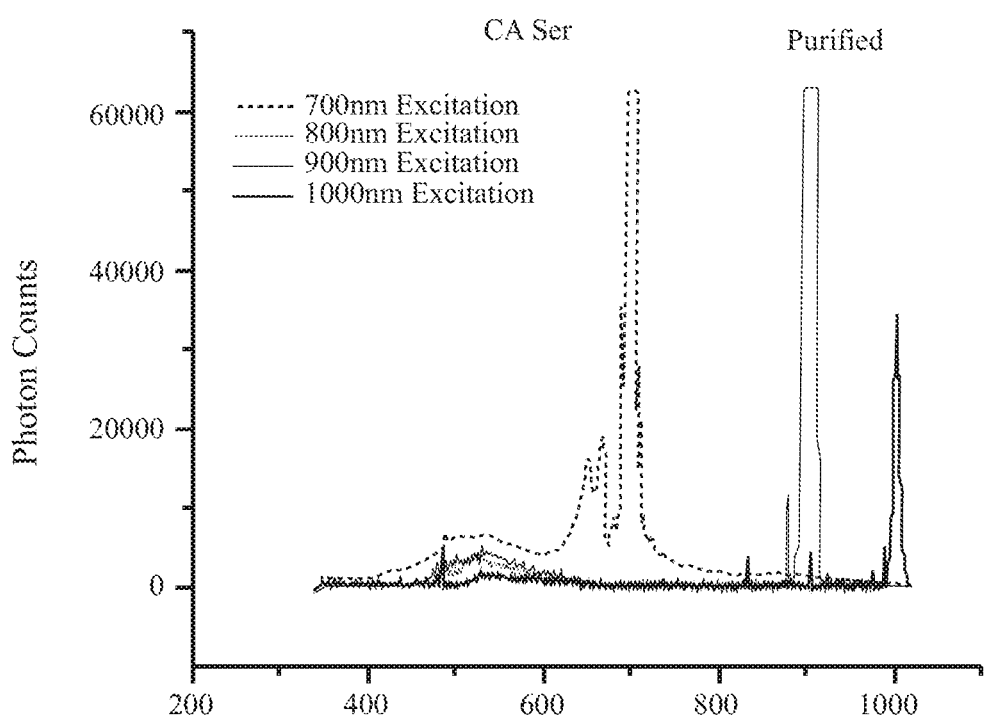
Figure 6C:
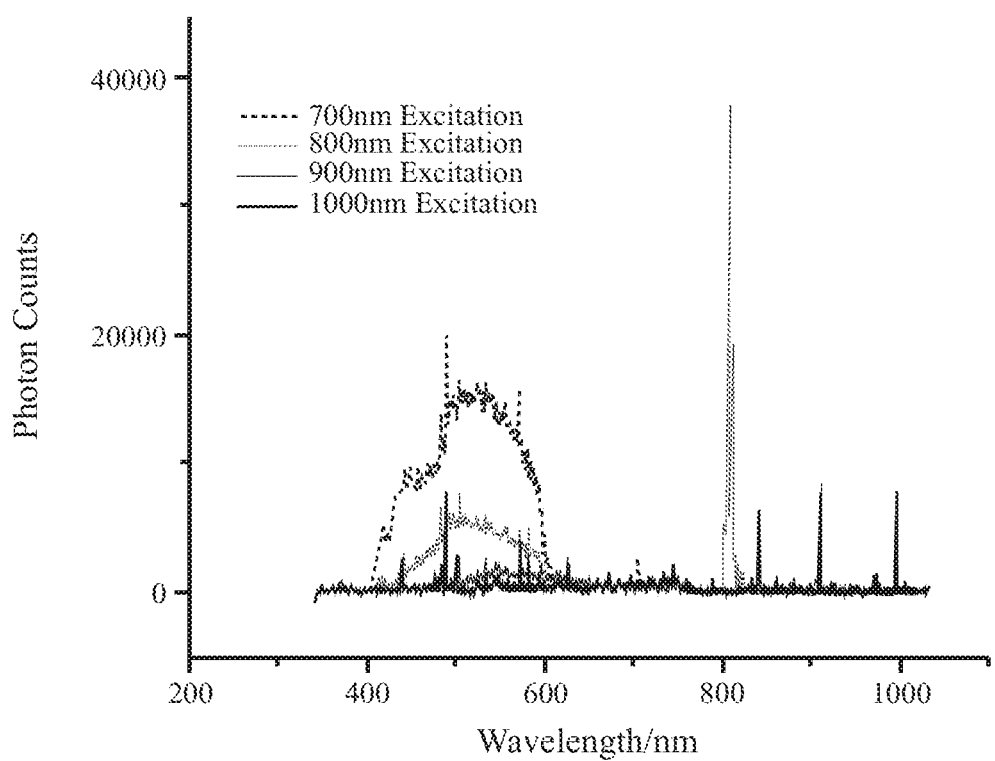
Figure 6D:
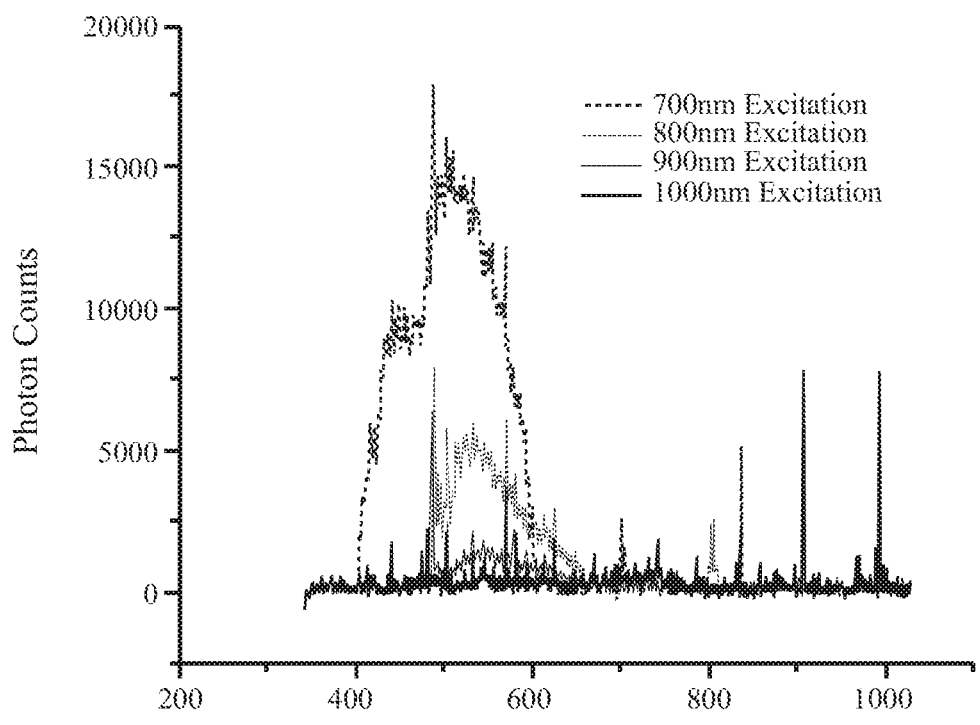
Figure 6G:
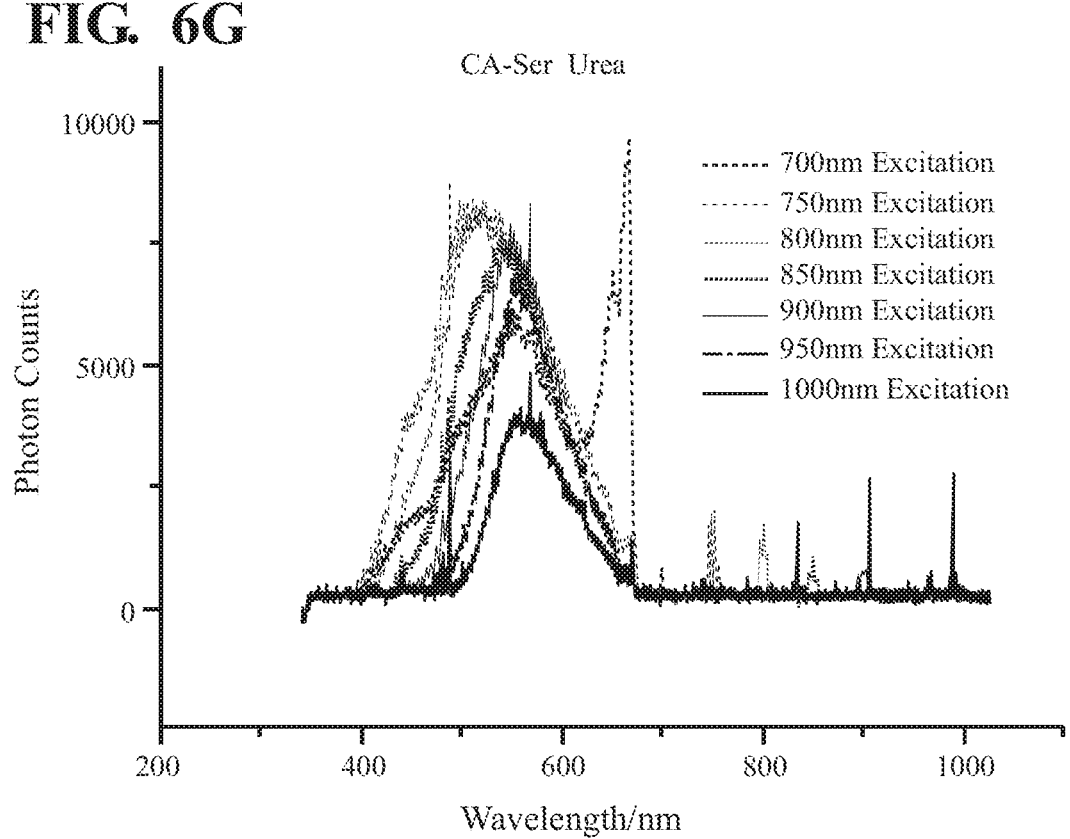
Figure 6H:
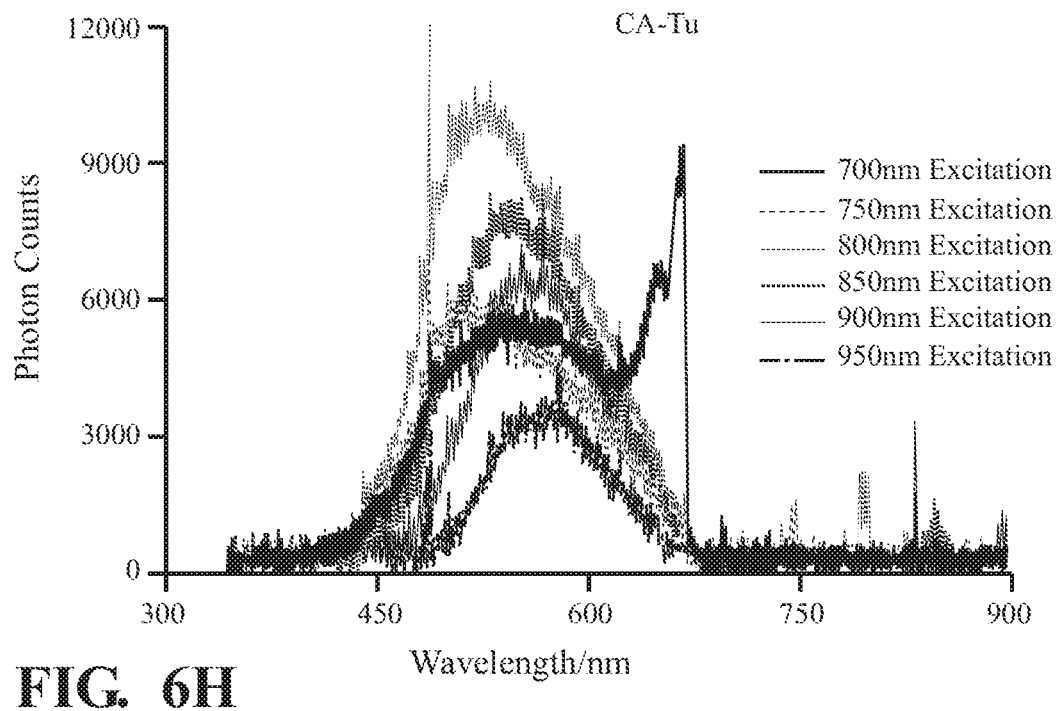

FIG. 4B is a detailed simulation flow chart for the determination of lens material and focal lengths. Here, H is the beam height of the incident excitation beam, $H_{ex}$ and $A_{ex}$ are the beam height and propagation angle of the excitation beam at a point after the objective lens, and $H_{em}$ and $A_{em}$ are the beam height and propagation angle of the fluorescence right after $L_4$. $M_1$, $M_3$, $M_5$, $M_8$, and $M_{10}$ represent the ABCD matrix of $L_1$, $L_2$, objective lens, $L_3$, and $L_4$, respectively. $M_2$, $M_4$, $M_6$, $M_7$, and $M_9$ represent the ABCD matrices of the corresponding free space propagation.

The lens properties of $L_1$ and $L_2$ can be determined from the desired axial imaging range. Then the axial focal positions and focusing angles of the three excitation wavelengths after the objective can be obtained by performing the ray tracing analysis for the excitation path. Based on the assumptions, the emitted fluorescence has the same longitudinal (or axial) focal positions and propagation angles as the corresponding excitation beams. Then the ray tracing analysis is performed again to determine the lens properties of $L_3$ and $L_4$ by minimizing the fluorescence propagation angle after $L_4$. Therefore, the collimated fluorescence can be focused into a single-mode fiber (or a pinhole) and directed to a spectrometer or an array of wavelength-selective detectors for spectral analysis.

One-Photon and Two-Photon Excitation Fluorescence Characterization:

Several candidates of band-shifting imaging probes including CA-Ser, CA-Asp Acid, CA-Ala and CA-Tu have been synthesized, by dissolving 50 mM citric acid and 50 mM of a primary amine or amino acid into 20 mL of DI water in a flask. The reaction was conducted at 140° C., open cap, until water mostly evaporated, followed by applying vacuum for 4 h. Afterwards, the reaction was terminated by adding 25 mL cold DI water to dissolve the products. Biodegradable photoluminescent polymers (BPLPs) were synthesized as follows. 100 mM citric acid, 100 mM 1,8-octanediol, and 20 mM of a primary amine or amino acid were reacted in a flask at 140° C. under nitrogen flow for 2 h. Next, 50 mL 1,4-dioxane was added to terminate the reaction and dissolve the resulting polymer, followed by precipitation in DI water and lyophilization for purification. CA-Ser Urea was synthesized by dissolving 0.5 g CA-Ser and 1.0 g urea into 5 mL N,N-Dimethylformamide (DMF) in a flask. The reaction was conducted at 160° C. with stirring and reflux for 4 h. One-photon fluorescence spectra of these imaging probe candidate materials were recorded on a Horiba FluoroMax-4 spectrofluorometer. As can be seen in FIGS. 5A-5G, these probes, i.e., (A) CA-Ser, (B) CA-Serpurified, (C) CA-Asp Acid, (D) CA-Ala, (E) BPLP-Arg, (F) CA-Tu (G) CASer-Urea, exhibit band shifting properties.

Two-photon fluorescence spectra are shown in FIGS. 6A-6H. The fluorescence emission of CA Ser, CA Ser purified, CA Asp Acid, CA Ala, CA Ala base, BPLP Arg DMSO, CA-Ser Urea and CA-Tu at the excitation frequencies 700-1000 nm are each shown in FIG. 6a-6h respectively.

Figure 7:
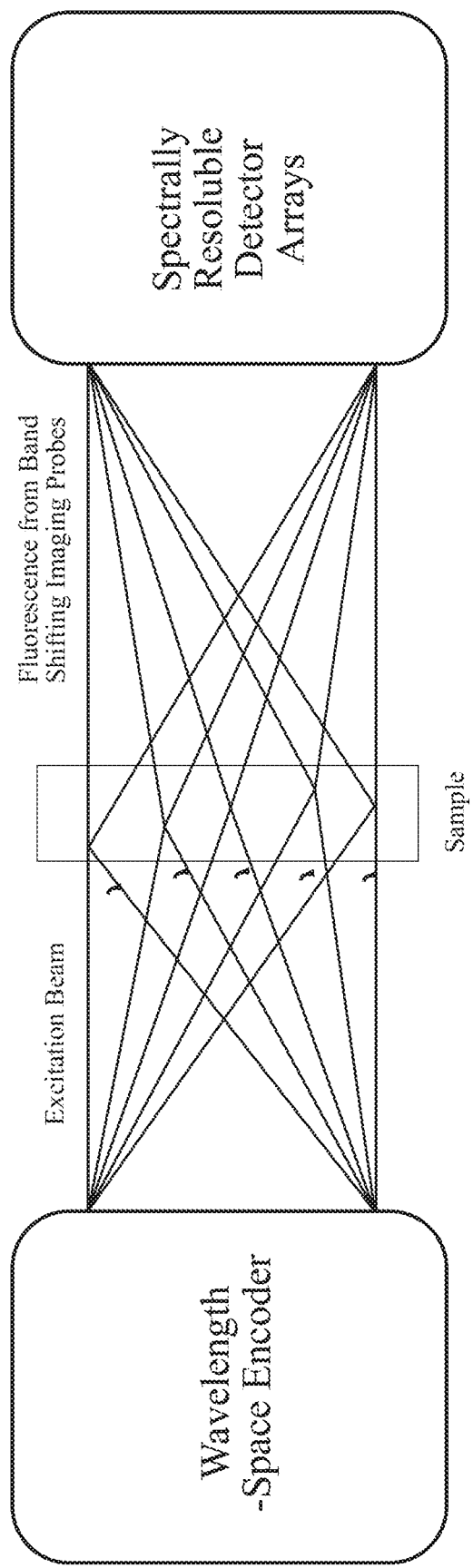
FIG. 7 shows a schematic of parallel imaging in three dimensions in accordance with an embodiment of the present invention.

FIG. 7 shows a schematic of parallel imaging in three dimensions in accordance with an embodiment of the present invention. In addition to parallel imaging in the axial and lateral directions, different wavelengths are mapped to locations in three dimensions. In this embodiment, it can be considered that the sample to be imaged is in an x-y-z coordinate, where the z-direction corresponds to the axial direction, i.e., the direction of the excitation beam and the x-y plane corresponds to the lateral direction, which is perpendicular to the axial direction. In FIG. 7, spectral encoding can be induced such that excitation beams are focused at different axial and lateral locations. As a result, parallel fluorescent imaging in three dimensions can be accomplished.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A spectrally encoded parallel fluorescence imaging system for imaging a sample, comprising:
   a multi-wavelength excitation light source emitting excitation light with a plurality of different wavelengths;
   optical components adapted for introducing spectral encoding in an axial direction such that the different wavelengths of the excitation light are focused at different axial positions in the sample and for introducing spectral coding in at least one lateral direction such that the different wavelengths of the excitation light are focused at different lateral positions in the sample thereby generating fluorescence signals emitted at the different axial and lateral positions, the axial direction coinciding or being parallel to an axis of the excitation light, the at least one lateral direction being perpendicular to the axis of the excitation light;
   band-shifting florescence imaging probes adapted for introduction into the sample, the band-shifting florescence imaging probes comprising fluorophores exhibiting excitation-dependent emission bands, each wavelength of the excitation light corresponding to a band-shifted fluorescence spectrum, thereby causing a different band-shifted fluorescence spectrum emitted at each of the different axial and lateral positions and transferring the spectral encoding of the excitation light to the fluorescence emission signals at the different axial and lateral positions of the sample, the fluorescence signals emitted at different axial and lateral locations of the labeled sample being already distinguished in center wavelengths at the sample through use of the band-shifting florescence imaging probes; and
   detectors operable to detect/collect different wavelengths for simultaneous detection/collection of the fluorescence signals emitted and already distinguished at the different axial and lateral positions of the sample, thereby enabling simultaneous recording of image signals of the sample at the different axial and lateral positions.

2. The spectrally encoded parallel fluorescence imaging system according to claim 1, wherein the fluorophores are cytocompatible biodegradable photoluminescent polymers (BPLPs).

3. The spectrally encoded parallel fluorescence imaging system according to claim 1, wherein the fluorophores are small molecular citrate-based photoluminescent dyes (CPDs) with identified structures of dioxopryridine (DPR).

4. The spectrally encoded fluorescence parallel imaging system according to claim 1, wherein the detectors are spectrometers, arrayed detectors or other wavelength-selective detectors.

5. The spectrally encoded parallel fluorescence imaging system according to claim 1, wherein the at least one lateral directions includes two orthogonal directions in an x-y plane in an x-y-z coordinate system such that the parallel fluorescence imaging in three dimensions is accomplished.

6. A method of spectrally encoded parallel fluorescence imaging for imaging a sample, the method comprising the steps of:
   labeling the sample with band-shifting florescence imaging probes, the band-shifting florescence imaging probes comprising a single type of fluorophores that exhibit excitation-dependent emission bands;
   providing a multi-wavelength excitation light source for fluorescent excitation of the labeled sample;
   introducing spectral encoding to the excitation light in an axial direction such that the different wavelengths of the excitation light are focused at different axial positions in the sample and spectral coding in at least one lateral direction such that the different wavelengths of the excitation light are focused at different lateral positions thereby generating fluorescence at the different axial and lateral positions, the axial direction coinciding or being parallel to an axis of the excitation light, the at least one lateral direction being perpendicular to the axis of the excitation light;
   generating fluorescence emission signal excited by the excitation light with the different wavelengths, and transferring the spectral encoding of the excitation light to the fluorescence emission signal at the different axial and lateral positions of the labeled sample, each wavelength of the excitation light corresponding to a different band-shifted fluorescence emission spectrum, the fluorescence signals emitted at different axial and lateral locations of the labeled sample being already distinguished in center wavelengths at the labeled sample; and
   detecting/collecting image information encoded in the already distinguished band-shifted fluorescence spectrums using detectors operable to detect different wavelengths, thereby simultaneously recording image signals of the sample at the different axial and lateral positions.

7. The method of claim 6, wherein the band-shifting fluorophores are biodegradable photoluminescent polymers (BPLPs) or molecular fluorescent probes.

8. The method claim 6, wherein the band-shifting fluorophores are small molecular citrate-based photoluminescent dyes (CPDs) with identified structures of dioxopryridine (DPR).

9. The method of claim 8, further comprising fine-tuning photophysical properties of the dyes for imaging optimization using a different selection of amine-containing molecules for DPR syntheses.

10. The method of claim 6, wherein the detectors are spectrometers, arrayed detectors or other wavelength-selective detectors.

11. The method of claim 6, wherein the fluorescence is generated in a two-photon excitation modality.

12. The method of claim 6, wherein the fluorescence is generated in a one-photon excitation modality.

13. The method of claim 12, further comprising collimating the fluorescence using chromatic aberration so that it can be confocally detected.

14. The method of claim 6, wherein the fluorescence is generated in a multi-photon excitation modality.

15. The method of claim 6, wherein the sample is a biological tissue or biological cells.

16. The method of claim 6, wherein introducing spectral encoding to the excitation light in the axial direction is by introducing axial chromatic aberration and introducing spectral encoding to the excitation light in the at least one lateral direction is by introducing lateral chromatic aberration.

17. A spectrally encoded endoscopy using a method in accordance with claim 6.

18. A parallel multi-photon fluorescence imaging system for imaging a sample, comprising:
- a multi-wavelength excitation light source emitting excitation light with a plurality of different wavelengths;
- optical components adapted for introducing spectral encoding such that the different wavelengths of the excitation light are focused at different spatial positions in the sample thereby generating fluorescence at the different spatial positions;
- band-shifting florescence imaging probes adapted for introduction into the sample, the band-shifting florescence imaging probes comprising fluorophores of a single type exhibiting excitation-dependent emission bands, each wavelength of the excitation light corresponding to a different band-shifted fluorescence spectrum, thereby causing a different band-shifted fluorescence spectrum emitted at each of the different spatial positions, and transferring the spectral encoding of the excitation light to the fluorescence emission signals at the different spatial positions of the sample, the fluorescence signals emitted at different spatial positions of the sample being already distinguished in center wavelengths at the sample through use of the band-shifting florescence imaging probes; and
- detectors operable to detect/collect different wavelengths for simultaneous non-confocal detection/collection of the fluorescence signals emitted and distinguished at the different spatial positions of the sample, thereby enabling parallel recording of image signals of the sample at the different spatial positions of the sample.

19. The parallel multi-photon fluorescence imaging system according to claim 18, wherein the non-confocal detection uses filters to resolve different wavelengths.

* * * * *